(12) United States Patent
Woods et al.

(10) Patent No.: US 9,299,117 B2
(45) Date of Patent: *Mar. 29, 2016

(54) METHOD AND SYSTEM FOR MANAGING INVENTORIES OF ORTHOPAEDIC IMPLANTS

(71) Applicant: DePuy Synthes Products, Inc., Raynham, MA (US)

(72) Inventors: Sherrod A. Woods, Fort Wayne, IN (US); Mark R. DiSilvestro, Columbia City, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/104,216

(22) Filed: Dec. 12, 2013

(65) Prior Publication Data

US 2014/0100886 A1    Apr. 10, 2014

Related U.S. Application Data

(63) Continuation of application No. 11/420,244, filed on May 25, 2006, now Pat. No. 8,635,082.

(51) Int. Cl.
| | |
|---|---|
| *G06Q 10/00* | (2012.01) |
| *G06Q 50/00* | (2012.01) |
| *G06Q 50/22* | (2012.01) |
| *G06F 19/00* | (2011.01) |

(Continued)

(52) U.S. Cl.
CPC .............. *G06Q 50/22* (2013.01); *G06F 19/321* (2013.01); *G06F 19/328* (2013.01); *G06Q 10/087* (2013.01); *A61F 2002/30953* (2013.01)

(58) Field of Classification Search
CPC ............................. G06Q 50/22; G06Q 50/24
USPC ......................................................... 705/2, 3
See application file for complete search history.

(56) References Cited

U.S. PATENT DOCUMENTS

| | | | |
|---|---|---|---|
| 6,692,448 B2 | 2/2004 | Tanaka et al. | |
| 6,711,432 B1 | 3/2004 | Krause et al. | |
| 6,786,930 B2 * | 9/2004 | Biscup | 623/16.11 |

(Continued)

OTHER PUBLICATIONS

Carter et al. The journal of Arthoplastry vol. 10 No. 4 1995, pp. 507-513.*

(Continued)

*Primary Examiner* — Neha Patel
(74) *Attorney, Agent, or Firm* — Barnes & Thornburg, LLP (57) ABSTRACT

A system and method for managing inventories of orthopaedic implants includes receiving a medical image of a bone of a patient from a healthcare provider, performing a digital templating procedure on the medical image to determine an orthopaedic implant for use with the bone of the patient; transmitting the digital templated medical image to the healthcare provider, and shipping the orthopaedic implant to the healthcare provider in response to an electronic approval of the digital templated medical image received from the healthcare provider. Implant constraint data may also be received from the healthcare provider and used in determining the orthopaedic implant. In addition, a number of orthopaedic implants having a range of different sizes based on the size of the determined orthopaedic implant may be shipped to the healthcare provider. In some embodiments, the healthcare provider may perform the digital templating procedure on the medical image.

7 Claims, 7 Drawing Sheets

(51) Int. Cl.
*G06Q 10/08* (2012.01)
*A61F 2/30* (2006.01)

(56) References Cited

U.S. PATENT DOCUMENTS 6,925,447 B2    8/2005   McMenimen et al.
7,340,316 B2 *  3/2008   Spaeth et al. ............. 700/98
2002/0007294 A1 * 1/2002   Bradbury et al. ............ 705/7
2002/0128651 A1    9/2002   Hyde
2002/0196344 A1 * 12/2002   McIntyre et al. ........ 348/207.1
2005/0149379 A1    7/2005   Cyr et al.

OTHER PUBLICATIONS

Carter et al., The Journal of Arthoplasty vol. 10, No. 4, 1995, pp. 507-513.

* cited by examiner

METHOD AND SYSTEM FOR MANAGING INVENTORIES OF ORTHOPAEDIC IMPLANTS

This application is a continuation application of U.S. patent application Ser. No. 11/420,244 entitled "Method and System for Managing Inventories of Orthopaedic Implants," which was filed on May 25, 2006 and is expressly incorporated herein by reference.

CROSS-REFERENCE TO RELATED U.S. PATENT APPLICATION

Cross-reference is made to U.S. Utility patent application Ser. No. 11/241,530 entitled "System and Method for Performing a Computer Assisted Orthopaedic Surgical Procedure," which was filed Sep. 30, 2005 by Mark R. DiSilvestro et al., the entirety of which is expressly incorporated herein by reference.

TECHNICAL FIELD

The present disclosure relates generally to systems and methods for managing inventories of orthopaedic implants.

BACKGROUND

Healthcare providers, such as surgeons, hospitals, and the like, typically must keep a broad selection of orthopaedic implant types and sizes in on-site inventories to ensure that the proper orthopaedic implant is available for a given orthopaedic surgical procedure. In addition, when the healthcare provider orders an orthopaedic implant from an orthopaedic implant manufacturer or distributor, the healthcare provider typically must order a broad selection of orthopaedic implant types and sizes.

Similarly, orthopaedic implant manufacturers and/or distributors typically must stock the complete line of orthopaedic implant types and sizes at each distribution center across a geographical region to ensure that the desired orthopaedic implants are available. As such, some orthopaedic implant manufacturers and/or distributors may stock large numbers of orthopaedic implant types and sizes even though some of the orthopaedic implant types and sizes may not be in high demand.

SUMMARY

According to one aspect, a method for managing inventories of orthopaedic implants includes transmitting a medical image of a patient's bone to a healthcare provider. For example, the medical image may be transmitted to the healthcare provider over a network. The medical image may be so transferred using any suitable communication protocol such as, for example a Digital Imaging and Communications in Medicine (DICOM) communication protocol. The medical image may include a digital template of an orthopaedic implant. The method may also include receiving an electronic approval of the medical image from the healthcare provider in response to the transmitting step. In addition, the method may include shipping the orthopaedic implant to the healthcare provider in response to the electronic approval. The method may further include receiving a medical image of the patient's bone from the healthcare provider and determining the orthopaedic implant from a number of orthopaedic implants based on the medical image prior to the transmitting step. Additionally or alternatively, a range of orthopaedic implant sizes may be determined. For example, a number of orthopaedic implant sizes within two sizes of a size of the orthopaedic implant may be determined. If so, a number of orthopaedic implants selected based on the range of orthopaedic implant sizes may be shipped to the healthcare provider.

Additionally, the method may include receiving implant constraint data from the healthcare provider. The orthopaedic implant may be determined based on the medical image and the implant constraint data. The method may also include generating the medical image of the patient's bone including the digital template of the orthopaedic implant based on the determined orthopaedic implant. Further, the method may include transmitting a purchase order for the orthopaedic implant to the healthcare provider and receiving an electronic authorization of the purchase order from the healthcare provider. The orthopaedic implant may be shipped to the healthcare provider in response to the electronic authorization.

According to another aspect, a system for managing inventories of orthopaedic implants includes a processor and a memory device electrically coupled to the processor. The memory device may have stored therein a plurality of instructions, which when executed by the processor, cause the processor to transmit a medical image of a patient's bone to a healthcare provider. The medical image may be transmitted over a network using any suitable communication protocol such as, for example a Digital Imaging and Communications (DICOM) in Medicine communication protocol. The medical image may include a digital template of an orthopaedic implant. The plurality of instructions may also cause the processor to receive an electronic approval from the healthcare provider in response to the medical image including the digital template and generate a shipping order for the orthopaedic implant to the healthcare provider in response to the electronic approval. Additionally, the plurality of instructions may cause the processor to receive a medical image of the patient's bone from the healthcare provider and determine the orthopaedic implant from a number of orthopaedic implants based on the medical image prior to transmitting the medical image including the digital template. Additionally or alternatively, the processor may determine a range of orthopaedic implant sizes. For example, the plurality of instructions may cause the processor to determine a number of orthopaedic implant sizes within two sizes of a size of the orthopaedic implant. If so, the generated shipping order may include a number of orthopaedic implants selected based on the range of orthopaedic implant sizes.

The plurality of instructions may yet further cause the processor to receive implant constraint data from the healthcare provider. If so, the orthopaedic implant may be determined based on the medical image and the implant constraint data. In addition, the plurality of instructions may cause the processor to generate the medical image of the patient's bone including the digital template of the orthopaedic implant based on the determined orthopaedic implant.

According to yet another aspect, a method for managing inventories of orthopaedic implants may include performing a digital templating procedure on a medical image of a patient's bone and determining an orthopaedic implant for use with the patient's bone based on the performing step. In addition, the method may include receiving an electronic approval from a healthcare provider and shipping the orthopaedic implant to the healthcare provider in response to the receiving step. The method may further include receiving the medical image of the patient's bone from the healthcare provider prior to the performing step and receiving implant constraint data from the healthcare provider. If so, the orthopaedic implant for use with the patient's bone may be determined based on the performing step and the implant constraint data. In addition, determining the orthopaedic implant may include determining a range of orthopaedic implant sizes. For example, a number of orthopaedic implant sizes within two sizes of a size of the orthopaedic implant may be determined. If so, a number of orthopaedic implants selected based on the range of orthopaedic implant sizes may be shipped to the healthcare provider. The method may further include transmitting a purchase order for the orthopaedic implant to the healthcare provider and receiving an electronic authorization of the purchase order from the healthcare provider. The orthopaedic implant may be shipped to the healthcare provider in response to the electronic authorization and the electronic approval.

According to a further aspect, a method for managing inventories of orthopaedic implants includes receiving a medical image of a patient's bone. The medical image may include a digital template of an orthopaedic implant. The method may also include determining a range of orthopaedic implant sizes based on the medical image. Additionally, the method may include receiving an electronic approval of the medical image from a healthcare provider. Further, the method may include shipping a number of orthopaedic implants selected based on the range of orthopaedic implant sizes to the healthcare provider in response to the electronic approval.

BRIEF DESCRIPTION OF THE DRAWINGS

The detailed description particularly refers to the following figures, in which:

FIG. 2a-2b is a simplified flowchart of an algorithm for managing inventories of orthopaedic implants used by the system of FIG. 1;

FIG. 4a-4b is a simplified flowchart of an algorithm for managing inventories of orthopaedic implants used by the system of FIG. 3.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Figure 1:
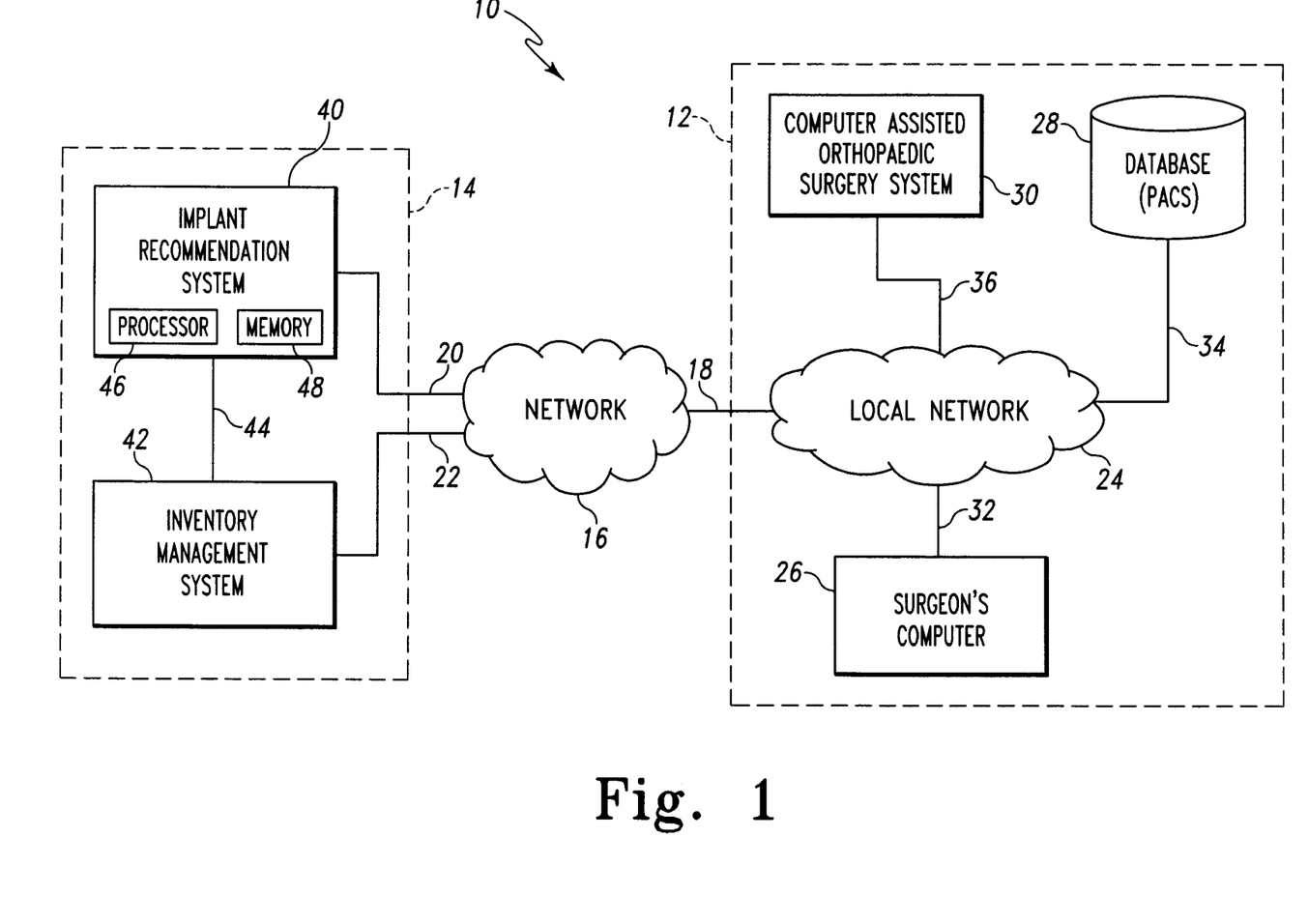
FIG. 1 is a simplified block diagram of a system for managing inventories of orthopaedic implants.

Referring to FIG. 1, a system 10 for managing inventories of orthopaedic implants includes a healthcare provider network 12 and an orthopaedic implant manufacturer and/or distributor network 14. The healthcare provider network 12 and the orthopaedic implant manufacturer network 14 are communicatively coupled to each other via a communication network 16 an a number of communication links 18, 20, 22. The network 16 may be embodied as any type of communication network capable of providing communication between the networks 12, 14. For example, the network 16 may be embodied as a wide area network (WAN), a local area network (LAN), or form a portion of a publicly-accessible, global network such as, for example, the Internet. In addition, the network 16 may be a wired network, a wireless network, or a combination thereof. As such, the network 16 may include any number of devices for providing communication between the networks 12, 14 such as routers, switches, computers, communication links, and the like. Similarly, the communication links 18, 20, 22 may be embodied as any type of communication links capable of providing communication between the networks 12, 14. For example, the communication links 18, 20, 22 may be embodied as any number of cables, wires, fiber optic cables, wireless signals, and/or the like.

The healthcare provider network 12 illustratively includes a local network 24, one or more orthopaedic surgeon's computer 26, a medical image database 28, which may be embodied as a Patient Archiving Communications System (PACS), and one or more computer assisted orthopaedic surgery systems (CAOS) 30. The local network 24 is communicatively coupled to the network 16 via the communication link 18. The local network 24 may be embodied as any type of network capable of providing communication between the computer(s) 26, the database 28, the computer assisted surgery system(s) 30, and/or the network 16. For example, the network 24 may be embodied as a wide area network (WAN), a local area network (LAN), a wireless WAN or LAN network, or the like and may include any number of devices for providing such communication such as routers, switches, computers, communication links, and the like.

The surgeon's computer 26 is communicatively coupled to the local network 24 via a communication link 32. The database 28 is communicatively coupled to the local network 24 via a communication link 34 and the computer assisted orthopaedic surgery system 30 is communicatively coupled to the local network 24 via a communication link 36. The communication links 32, 34, 36 may be embodied as any type of communication links capable of providing communication between the computer(s) 26, the database 28, and the system(s) 30 and the local network 24. For example, the communication links 32, 34, 36 may be embodied as any number of cables, wires, fiber optic cables, wireless signals, and/or the like.

The surgeon's computer(s) 26 may be embodied as any type of computer or computing device capable of displaying data to a surgeon and receiving input from the surgeon. For example, the computer(s) 26 may be embodied as a typical desktop or laptop computer equipped with a display screen, keyboard, and other devices and circuitry typically found in a desktop and/or laptop computer. Although illustrated in FIGS. 1 and 3 as forming part of the hospital network 12, in some embodiments, the surgeon's computer 26 may be remotely located from the hospital facility. For example, the surgeon's computer 26 may be located in the surgeon's office, which may be located remotely from the hospital facility. In such an embodiment, the surgeon's computer 26 is commutatively coupled to the hospital network 12 via the network 24 and/or the network 16.

The database 28 may be embodied as any type of database capable of storing a number of medical images and associated data. For example, the database 28 may be embodied as any number of separate databases, file folders, file storage locations with associated look-up tables, flat files, or the like. In addition, the database 28 may include any number of storage devices for storing any number of individual databases that form the database 28. In one particular embodiment, the database 28 is embodied as a Patient Archiving Communications System (PACS), but in other embodiments other types of databases may be used. The computer assisted orthopaedic surgery system(s) 30 may be embodied as any type of computer assisted orthopaedic surgery system. Illustratively, the CAOS system 30 is embodied as one or more computer assisted orthopaedic surgery systems commercially available from DePuy Orthopaedics, Inc. of Warsaw, Ind. and/or one or more computer assisted orthopaedic surgery systems commercially available from BrainLAB of Heimstetten, Germany.

As discussed above, the computer(s) 26, the database 28, and/or the CAOS system 30 may communicate with each other and/or with the communication network 16 via the local network 24. For example, the surgeon's computer 26 may be used to access data, such as medical images, stored on the database 28. Additionally or alternatively, the computer assisted orthopaedic surgery system 30 may be used to generate pre-operative orthopaedic surgical plans, surgical notes created during an orthopaedic surgery, medical images of a patient's bone (and soft tissue) and/or orthopaedic implants coupled thereto, and/or other data. Such data generated via the CAOS system 30 may be stored in the database 28 by, for example, transmitting the data from the system 30 to the database 28 via the network 24. Additionally, other medical devices typically found in a hospital or other healthcare facility may be used to generate medical images of a bone (and, in some embodiments, soft tissue) of the patient. Such medical images may also be stored in the database 28. The medical images may be embodied as any type of medical image providing a visual indication of a relevant bone or bones (and soft tissue if desired) of a patient. For example, the medical images may be embodied as any number of X-ray images, magnetic resonance imaging (MRI) images, computerized tomography (CT) images, or the like. Regardless, such medical images may be stored in the database 28 along with associated data relevant to the particular medical images. Such associated data may include, but is not limited to, the patient's name and other patient identification information, date of the images, surgeon's or doctor's name, the name of the hospital or healthcare facility wherein the medical images were generated, and the like.

Turning now to the orthopaedic implant manufacturer network 14, the network 14 includes an implant recommendation system 40 and an inventory management system 42. The systems 40, 42 are coupled to each other via a communication link 44 and to the communication network 16 via communication links 20, 22, respectively. The communication link 44 may be similar to the communication links 20, 22 and may be embodied as any type of communication link capable of providing communication between the implant recommendation system 40 and the inventory management system 42. For example, the communication link 44 may be embodied as any number of wires, cables, fiber optic cables, wireless signals, or the like.

Figure 2A:
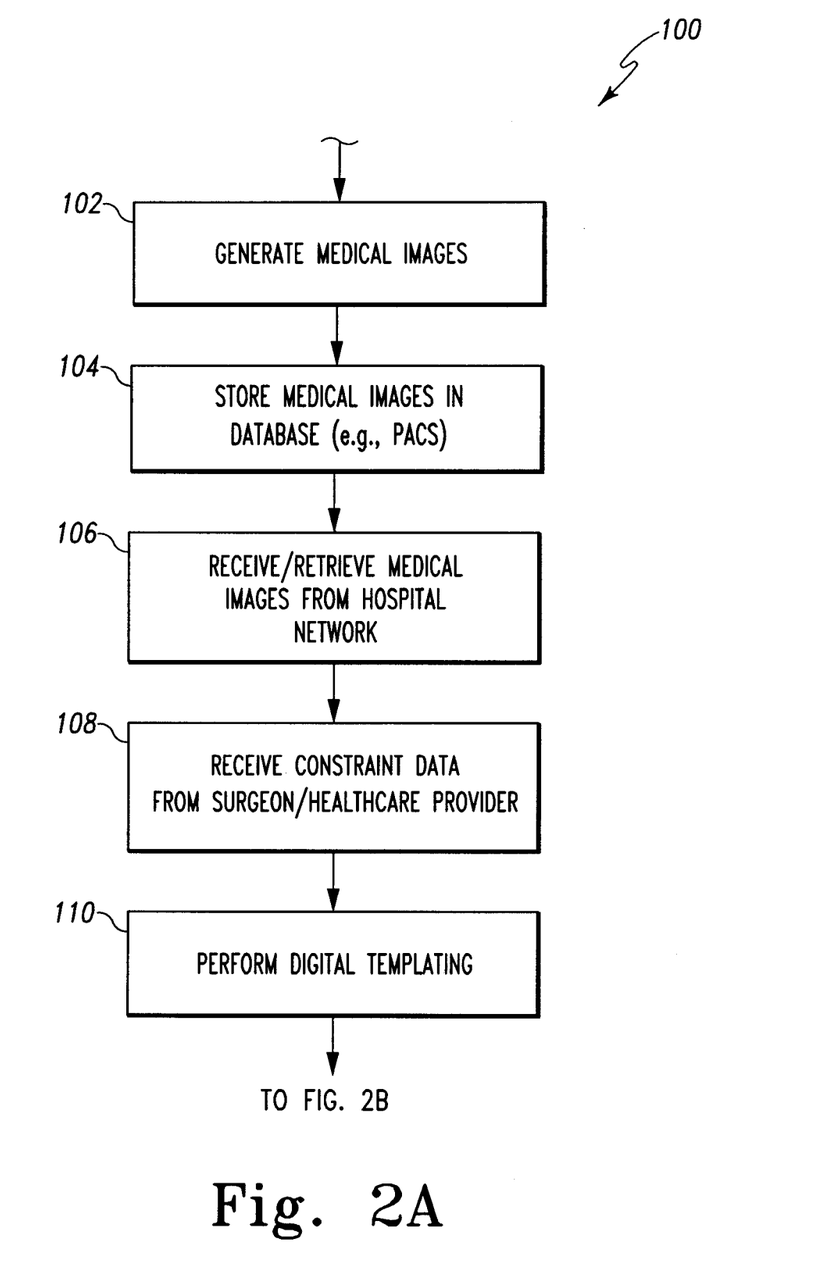
Figure 2B:
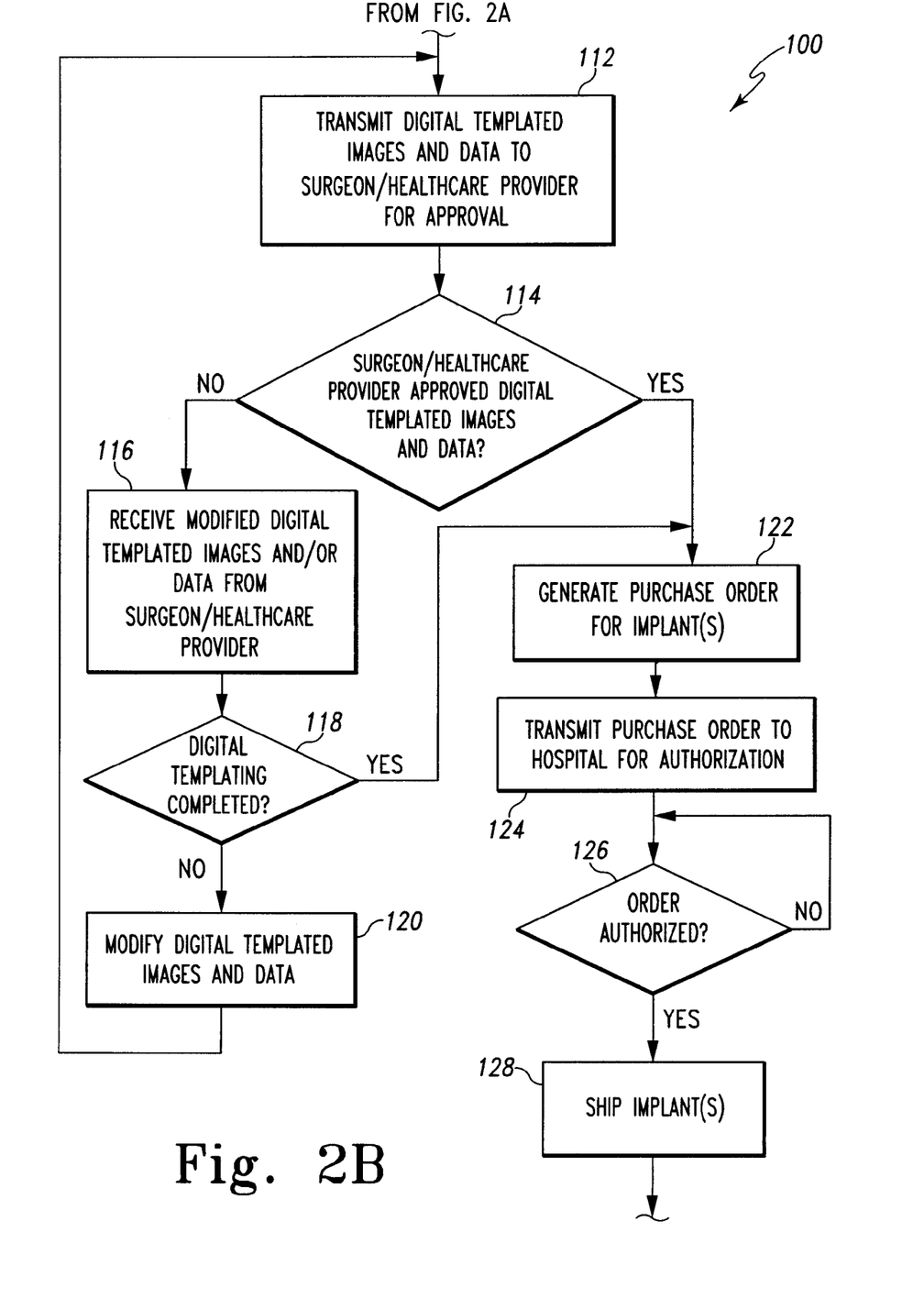

The implant recommendation system 40 may be embodied as any number of computers and/or computing devices, and associated software, middleware, and/or firmware, configured to perform the implant recommendation functions described herein. For example, the system 40 may include any number of computers and/or computing devices configured to receive medical images from the hospital network 12, perform a digital templating procedure on the medical images to determine one or more orthopaedic implants based thereon, transmit the digital templated medical images back to the hospital network, and receive an electronic approval of the images from the hospital network as discussed in more detail below in regard to FIGS. 2a-2b.

The illustrative implant recommendation system 40 is embodied as one or more computers and/or computing devices having one or more processors 46 and one or more memory device 48. The processor 46 may be embodied as any type of processor including, for example, discrete processing circuitry (e.g., a collection of logic devices), general purpose integrated circuit(s), and/or application specific integrated circuit(s) (i.e., ASICs). The memory device 48 may be embodied as any type of memory device and may include one or more memory types, such as, random access memory (i.e., RAM) and/or read-only memory (i.e., ROM). In addition, the implant recommendation system 40 may include other devices and circuitry typically found in a computer for performing the functions described herein such as, for example, a hard drive, a display and associated driver circuitry, input/output circuitry, and the like.

Similarly, the inventory management system 42 may be embodied as any number of computers or computing devices, and associated software and/or firmware, configured to perform the inventory management functions described herein. For example, the system 42 may include any number of computers and/or computing devices configured to receive an electronic order from the implant recommendation system, transmit a purchase order to the hospital network, receive an electronic authorization of the purchase order from the hospital network, and generate a shipping order to cause a number of orthopaedic implants to be shipped to the healthcare provider as discussed in more detail below in regard to FIGS. 2a-2b. As such, the inventory management system 42 may include one or more computers, display devices, printers, communication devices and links, and/or the like. For example, in some embodiments the inventory management system 42 may include a remote computer located at a number of distribution or shipping centers. Such remote computers may be communicatively coupled to a central computer or computing device and configured to receive the shipping orders therefrom.

Although illustrated in FIG. 1 as separate systems, in some embodiments, the implant recommendation system 40 and the inventory management system 42 are embodied as a single system. For example, the systems 40, 42 may be embodied as software algorithms stored on and executed by one or more computers communicatively coupled together.

In operation, the system 10 may be used to determine orthopaedic implants for use in an orthopaedic surgical procedure and ship such orthopaedic implants to the healthcare provider in an automated manner. To do so, as illustrated in FIGS. 2a and 2b, an algorithm 100 for managing inventories of orthopaedic implants may be used. The algorithm 100 begins with process step 102 in which medical images of a relevant bone or bones of a patient are generated. Typically, the medical images are generated pre-operatively in preparation for an orthopaedic surgical procedure. The medical images may include any number of medical images. For example, the medical images may include a medical image of the relevant bone(s) taken along the sagittal plane of the patient's body and a medical image of the relevant bone(s) taken along the coronal plane of the patient's body. As discussed above in regard to FIG. 1, the medical images may be embodied as any type of image capable of providing indicia of the relevant bone or bones. For example, the medical images may be embodied as any number of X-ray images, magnetic resonance imaging (MRI) images, computerized tomography (CT) images, or the like. As such, any number of imaging devices and systems, such as an X-ray machine, a CT scanner, and/or an MRI machine may be used to generate the medical images. Such imaging devices may be located in the healthcare facility of the hospital network 12 or may be located remote therefrom. The imaging devices may or may not be communicatively coupled to the hospital network 12.

In process step 104, the medical images are stored in the database 28. As discussed above in regard to FIG. 1, in some embodiments such as those embodiments wherein the database 28 is embodied as a PACS system, the medical images are stored in the database 28 in association with metadata. The metadata may include any type of data capable of being stored in the database 28 and associated with the particular medical images. For example, the metadata may include the patient's name, address, and/or other patient identification data, the surgeon's name or identifier, the healthcare facility's name or identifier, and/or any other type of data useful in determining an orthopedic implant for use with the relevant imaged bone(s). In embodiments wherein the imaging device forms a portion of the hospital network 12, the medical images may be stored in the database 28 by transmitting the medical images to the database 28 via the local network 24.

Subsequently, in process step 106, the medical images and any associated metadata are received by the implant recommendation system 40 of the orthopaedic implant manufacturer network 14. To do so, the surgeon or other healthcare provider may transmit the medical images and metadata from the database 28 to the implant recommendation system. Alternatively, in some embodiments, the implant recommendation system 40 may be configured to communicate with the database 28 via the communication network 16 and the local network 24 to retrieve the medical images and associated metadata from the database 28. In such embodiments, the implant recommendation system 40 may be configured to retrieve medical images and metadata on a periodic basis or in response to an instruction or authorization received from the hospital network 12. For example, the implant recommendation system 40 may be configured to retrieve the medical images and associated metadata from the database 28 in response to an electronic authorization received from the hospital network 12 via the network 16. The electronic authorization may include, for example, the location of the medical images and metadata in the database 28, instructions on how to access the medical images and metadata, authorization to retrieve the medical images and metadata, and/or the like. Regardless, the medical images and any associated metadata are received by the implant recommendation system 40 in process step 106 and may be stored in, for example, the memory device 48 or other memory storage location of the implant recommendation system 40.

In addition to the medical images and associated metadata, implant constraint data is received by the implant recommendation system 40 from the surgeon or other healthcare provider in process step 108. The implant constraint data may be embodied as any additional data that may limit, restrict, or otherwise affect the selection of an orthopaedic implant for use with the bone(s) of the patient depicted in the medical images. For example, the implant constraint data may include the surgeon's preference for an orthopaedic implant type, the surgeon's preference for particular parts of the implant, the degree of acceptable orthopedic implant sizes (e.g., a restriction on the range of implant sizes that may be recommended), the amount of bone that will be resected, the planned location and/or orientation of the orthopaedic implant, fixation type (e.g., cement or cementless), material type, finish, and other features such as head size and other preferences such as metal-on-metal, metal-on-ceramic, ceramic-on-ceramic, metal-on-poly, or the like. In some embodiments, the constraint data may form a portion of the metadata and be stored in the database 28 in association with the relevant medical images. In other embodiments, the surgeon or other healthcare provider may transmit the implant constraint data to the implant recommendation system 40 separate from the medical images.

Once the medical images, associated metadata, and any implant constraint data are received by the implant recommendation system 40, the system 40 performs a digital templating procedure on the medical images in process step 110 to determine an orthopaedic implant to recommend to the surgeon or healthcare provider for use with relevant bone(s) of the patient. To do so, the implant recommendation system 40 may be configured to determine relevant aspects of the patient's bone or bony anatomy from the medical images. For example, the implant recommendation system 40 may determine one or more mechanical axis of the relevant bones, determine one or more resection planes of the relevant bones, locate particular features of the relevant bones, and/or the like. Based on such determinations, the implant recommendation system 40 is configured to select an appropriate orthopaedic implant type and size that also satisfies the implant constraint data received from the surgeon in process step 108. The implant recommendation system 40 may also be configured to determine recommended range of sizes of the orthopaedic implant. For example, in some embodiments, the implant recommendation system 40 may be configured to determine a recommended orthopaedic implant within a range of plus or minus two sizes. For example, the implant recommendation system 40 may recommend an orthopaedic implant of a size 5+/−2 sizes (i.e., a range of size 3 to size 7).

Once the appropriate orthopaedic implant has been selected, the implant recommendation system 40 retrieves a digital template(s) of the orthopaedic implant. The digital template may be retrieved from, for example, the memory device 48 or from any other storage location capable of storing a number of digital templates. As used herein, the term "digital template" is defined as one or more two-dimensional and/or three-dimensional electronic renderings of an orthopaedic implant, or components thereof, that is capable of being superimposed on a medical image of a patient. For example, a digital template may be embodied as a two-dimensional or three-dimensional electronic rendering of an orthopaedic knee implant component that is capable of being superimposed or otherwise incorporated into a medical image of a tibia or femur bone of the patient. As discussed in more detail below, the digital template may be used in conjunction with indicia of the determined aspects or features of the relevant bones such as lines or other indicia of the mechanical axis or resection points/planes of the relevant bones.

Figure 5:
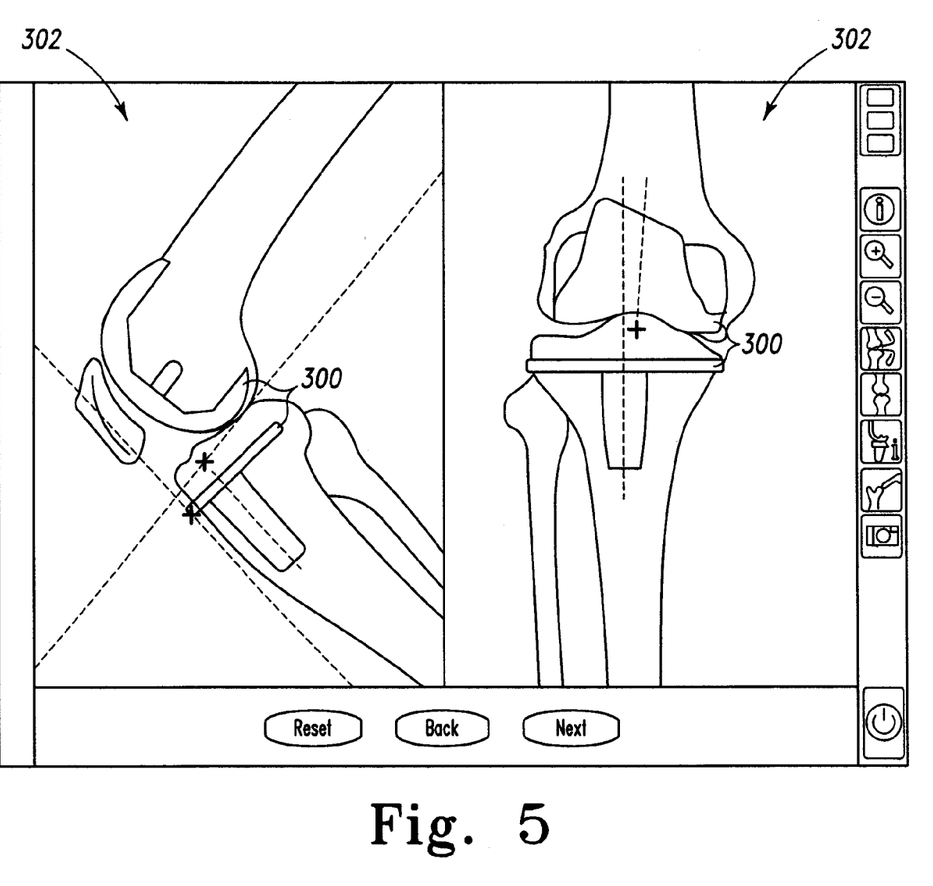
FIG. 5 is an illustrative screen display of a medical image having a digital template of an orthopaedic implant superimposed thereon.

Once the digital template(s) of the recommended orthopaedic implant has been retrieved from storage, the implant recommendation system 40 is configured to superimpose or otherwise incorporate the digital template into the medical images received from the hospital network in process step 106. For example, in one illustrative embodiment, as illustrated in FIG. 5, a digital template 300 of an orthopaedic implant is superimposed on a medical image 302 of a bone of a patient. During the digital templating process, the digital template 300 may be positioned in any location and orientation relative to the medical image 302. As discussed above, although the illustrative digital template 300 is illustrated as a two-dimensional template, in other embodiments, the digital template may include any number of two-dimensional and/or three-dimensional electronic renderings of the orthopaedic implant.

The system 40 may be configured to use any suitable algorithm (and the implant constraint data in some embodiments) to determine a recommended location and orientation of the orthopaedic implant, as represented by the digital template, with respect to the patient's bone. For example, if implant constraint data provides an estimated amount of resection of the patients' bone, the implant recommendation system 40 may be configured to position the digital template in the medical images based on such estimated resection. In addition, any one or more of the aspects of the bone as determined above may be used to determine the proper positioning of the digital template. For example, the determined mechanical axis, resection planes, and/or other determined aspects of the relevant bones may be used to determined the proper positioning of the digital template. In this way, the orthopaedic implant recommendation system generates a number of digital templated medical images having indicia of the relevant bone's of the patient and indicia of the recommended orthopaedic implant positioned in a location and orientation.

It should be appreciated that the implant recommendation system 40 may use any one or more of a number of systems and/or algorithms to perform the digital templating procedure on the medical images. For example, in one illustrative embodiment, the system and algorithm used to perform the digital templating procedure is embodied as an iPLAN® digital templating system, which is commercially available from BrainLAB of Heimstetten, Germany.

In addition, although described above as an automated process, in some embodiments, the digital templating procedure performed in process step 110 may be a semi-automated or a manual process. For example, in embodiments utilizing a semi-automated digital templating procedure, a technician such as a CAD operator or medical technician may determine the aspects of the relevant bones such as the mechanical axis, the resection lines, and/or other particular features of the relevant bones. The technician may edit the medical images such that indicia of such aspects are superimposed or otherwise incorporated into the medical images. For example, the technician may electronically draw the mechanical axes and/or resection lines. Once such aspects of the relevant bones are determined, the recommendation system 40 may be configured to determine a recommended orthopaedic implant based on the aspects of the relevant bones determined by the technician, retrieve a digital template of the recommended orthopaedic implant, and superimpose or otherwise incorporate the digital template into the medical image based on, for example, the determined aspects of the relevant bones.

In other embodiments, a manual digital templating process may be used in process step 110. In such embodiments, a technician may determine the aspects of the relevant bones, incorporate indicia of such aspects into the medical images (e.g., draw the mechanical axis, resection lines, etc. of the relevant bones), and determine a recommended orthopaedic implant based on such aspects. The technician may then manually superimpose or otherwise incorporate a digital template of the recommended orthopaedic implant into the medical images. The technician may locate and orientate the digital template based on the determined aspects of the relevant bones. For example, the technician may position the digital template of the recommended orthopaedic implant in the medical image using a suitable CAD software program or the like.

Regardless, once the digital templating process is complete, the implant recommendation system 40 transmits the digital templated medical images and any other implant recommendation data (e.g., the recommended range of implant sizes) to the healthcare provider via the communication network 16 and the local network 24 in process step 112. Once received, the digital templated medical images may be stored, for example, in the database 28 and/or in the surgeon's computer 26, or other data storage location. Subsequently, in process step 114, the orthopaedic surgeon reviews the digital templated medical images and determines if he/she approves of the recommended orthopaedic implant type and size(s) based on the digital templated medical images and implant recommendation data. For example, the surgeon may review the digital templated medical images to determine if the digital template of the orthopaedic implant is properly located with respect to the patient's bone, if the type of recommended orthopaedic implant is correct, if a larger or smaller orthopaedic implant size is more desirable, and/or the like.

If the surgeon decides that the digital templated medical images and/or recommendation data is not correct, the surgeon may modify the digital templated medical images and/or data and transmit the modified digital templated medical images and/or data to the implant recommendation system 40 in process step 116. To do so, the surgeon may, for example, operate the computer 26 and/or the computer assisted orthopaedic surgery system 30 to relocate the digital template of the orthopaedic implant on the medical images. Alternatively, the surgeon may select a different orthopaedic implant (e.g., a different orthopaedic implant type or size) and incorporate a digital template of the new orthopaedic implant in the medical images in place of the existing digital template. In this way, the surgeon may modify the digital templated medical images received from the implant recommendation system 40 until the orthopedic implant and position thereof is as desired by the surgeon. Once so modified, the surgeon may transmit the modified digital templated medical images and any associated recommendation data back to the implant recommendation system 40 in the process step 116.

Once the modified digital templated medical images are received by the implant recommendation system 40 in process step 116, the system 40 determines if the digital templating procedure is complete in process step 118. The system 40 may use any suitable algorithm or criteria to determine if the digital templating procedure is complete. For example, in some embodiments, the implant recommendation system 40 may determined if the digital template of the recommended orthopaedic implant is positioned in a valid location and orientation, if the orthopaedic implant selected by the surgeon is a valid orthopaedic implant type and/or size, if any additional adjusts to the digital templated medical images are required, and/or the like.

If the digital templating procedure is determined to be completed, the algorithm 100 advances to process step 122, which is described in detail below. However, if the digital templating procedure is not completed, the implant recommendation system 40 is configured to modify the digital templated medical images and implant recommendation data in process step 120. For example, if the digital template of the orthopaedic implant is determined to be in an invalid location in process step 118, the system 40 may be configured to adjust the digital template in process step 120. As such, it should be appreciated that the implant recommendation system 40 may perform any number of corrective procedures on the modified digital templated medical images and/or recommendation data (e.g., the range of recommended orthopaedic implant sizes) received from the surgeon in process step 120.

Once the digital templated medical images and/or recommendation data received from the surgeon in process step 116 have been modified in process step 120, the algorithm 100 loops back to process step 112 wherein the digital templated medical images and/or the recommendation data, including any adjusts thereto, are transmitted to the surgeon again. As such, the process steps 112, 114, 116, 118, 120 may be repeated until the digital templated medical images and/or recommendation data are as desired by the surgeon and/or determined completed by the implant recommendation system 40.

Referring now back to process step 114, if the surgeon approves the digital templated medical images and recommendation data, an electronic approval is transmitted to the implant recommendation system 40 in process step 114. The electronic approval may be embodied as any type of data transmittable over the network 16 and capable of providing notification to the systems 40, 42 that the digital templated medical images and recommendation data is approved by the surgeon. For example, the electronic approval may be embodied as an email, a predetermined response to the digital templated medical images, or any other data capable of providing notification of the approval to the implant recommendation system 40.

Once the electronic approval is received by the implant recommendation system 40, the algorithm 100 advances to process step 122. In process step 122, a purchase order of the recommended orthopaedic implant(s) is generated. The purchase order may be generated by either the implant recommendation system 40 or the inventory management system 42. For example, in some embodiments the implant recommendation system 40 is configured to transmit the recommended orthopaedic implant and range of sizes, if any, to the inventory management system 42 via the communication link 44 in process step 122. In response, the inventory management system 42 may be configured to generate the purchase order for the recommended orthopedic implant and any additional orthopedic implants as determined by the range of orthopaedic implant sizes.

Regardless, a purchase order for the orthopaedic implant(s) is generated in process step 122 and subsequently transmitted to the hospital network 12 for authorization in process step 124. The purchase order may be transmitted to the hospital network 12 via the communication links 20 or 22, the communication network 16, and the communication link 18. In one particular embodiment, the purchase order is transmitted to an individual, department, or other entity of the healthcare provider (e.g., the hospital) that is responsible for the payment of bills such as, for example, the accounts payable department of the healthcare provider. Additionally or alternatively, the purchase order may be transmitted to an individual or department that oversees or otherwise monitors orthopaedic surgeries. Regardless, the purchase order is transmitted to the hospital network 12 for authorization by the healthcare provider (e.g., the hospital, the surgeon, the accounts receivable department, or the like) in process step 124.

Once the purchase order has been transmitted to the healthcare provider, the implant recommendation system 40 and/or the inventory management system 42 waits for an electronic authorization from the healthcare provider. The electronic authorization may be embodied as any type of data transmittable over the network 16 and capable of providing notification to the systems 40, 42 that the purchase order is authorized. For example, the electronic authorization may be embodied as an email (e.g., a response to an email), a predetermined response to the purchase order, a voicemail authorization, or any other data capable of providing notification of the authorization to the implant recommendation system 40 and/or the inventory management system 42. In one embodiment, the purchase order transmitted to the healthcare provider in process step 124 may include an authorization button or other selection device. To authorize the shipment of the recommended orthopaedic implants, the healthcare provider may simply select the authorization button from the purchase order, which may be displayed on any available display device. In response to the selection by the healthcare provider, electronic authorization data may be transmitted to the systems 40, 42 via the communication network 16. In other embodiments, other methodology may be used Once the electronic authorization is received from the healthcare provider in process step 126, the orthopaedic implant(s) is timely shipped to the healthcare provider in process step 128. To do so, in some embodiments, the inventory management system 42 is configured to generate a shipping order based on the purchase order. The shipping order may include which orthopaedic implants to ship, the address of the healthcare provider, and any other information required to properly ship the orthopaedic implant(s) to the healthcare provider. In embodiments wherein the orthopaedic implant inventories of the orthopaedic implant manufacturer are distributed across a number of distribution centers, the inventory management system 42 may be configured to select the distribution center(s) to which the shipping order should be transmitted. For example, the inventory management system 42 may be configured to monitor the inventories of the distribution centers and transmit the shipping order, or portion thereof, to the distribution center(s) having the particular orthopedic implants in stock. Additionally or alternatively, the inventory management system 42 may be configured to transmit the shipping order, or portion thereof, to the nearest available distribution center to the healthcare provider to thereby improve the speed of delivery of the orthopaedic implants. Further, in some embodiments, the inventory management system 42 may be configured to track or otherwise record the orthopaedic implants ordered by each healthcare provider. In such embodiments, the inventories of orthopaedic implants may be adjusted at each distribution center based on the demand of particular orthopaedic implants by the healthcare provider commonly serviced by the particular distribution center.

Figure 3:
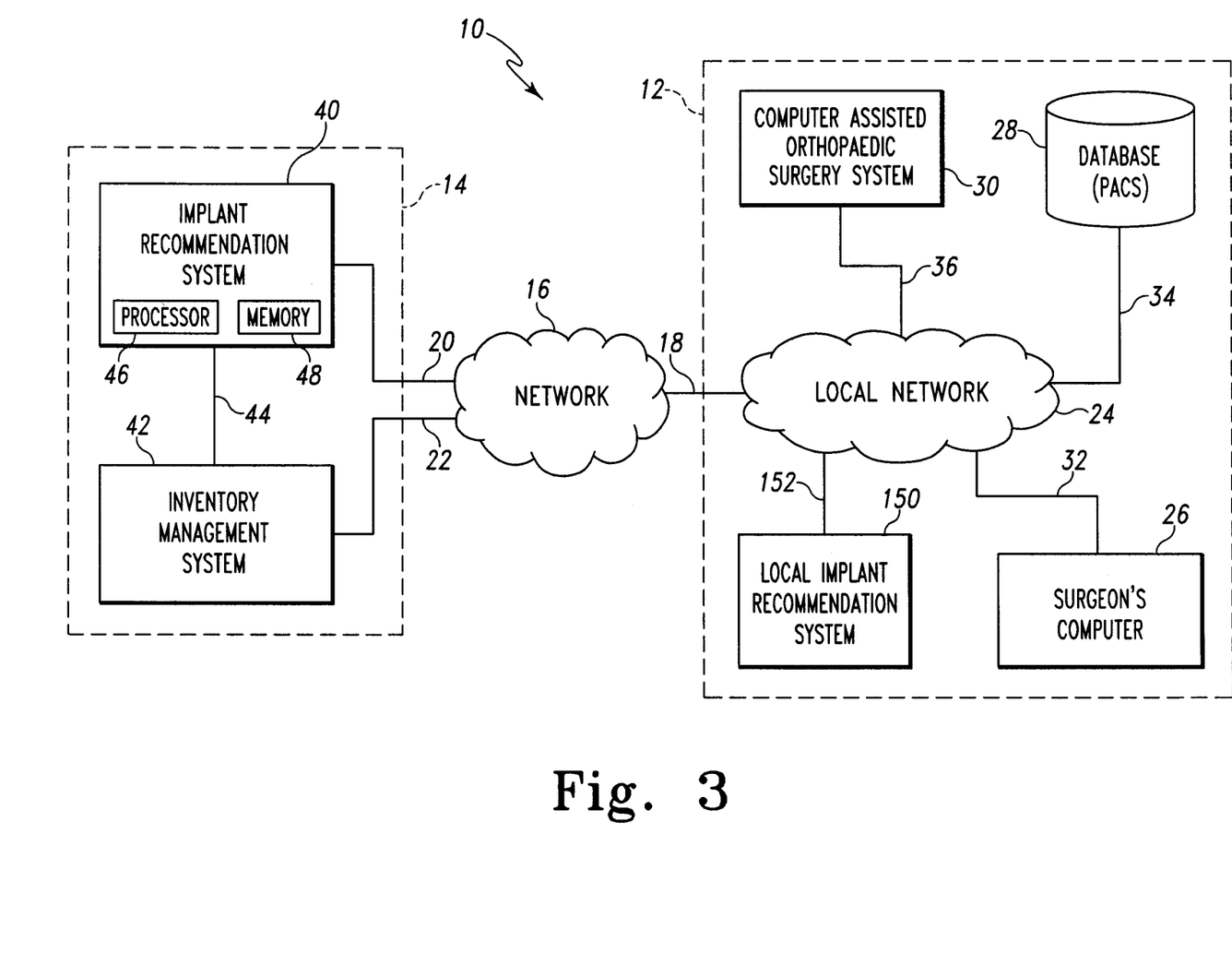
FIG. 3 is a simplified block diagram of another embodiment of a system for managing inventories of orthopaedic implants.
Figure 4A:
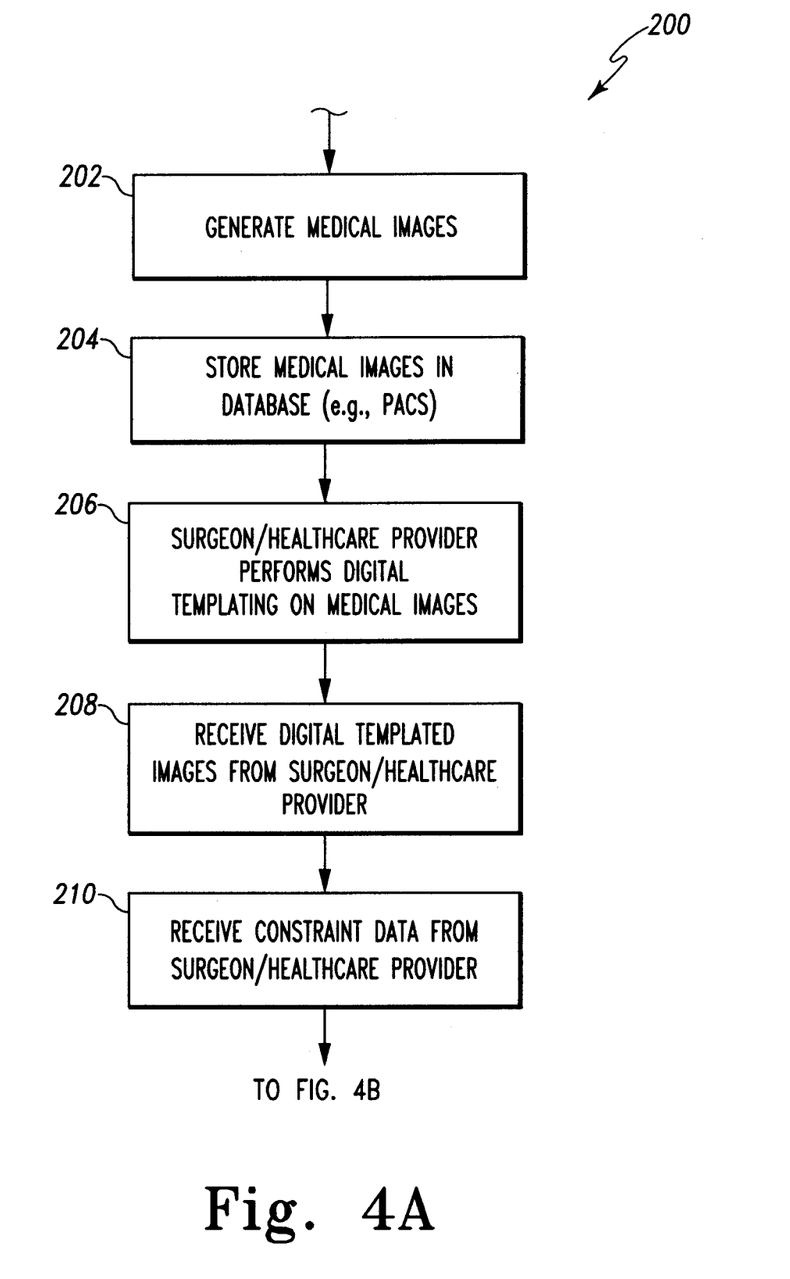
Figure 4B:
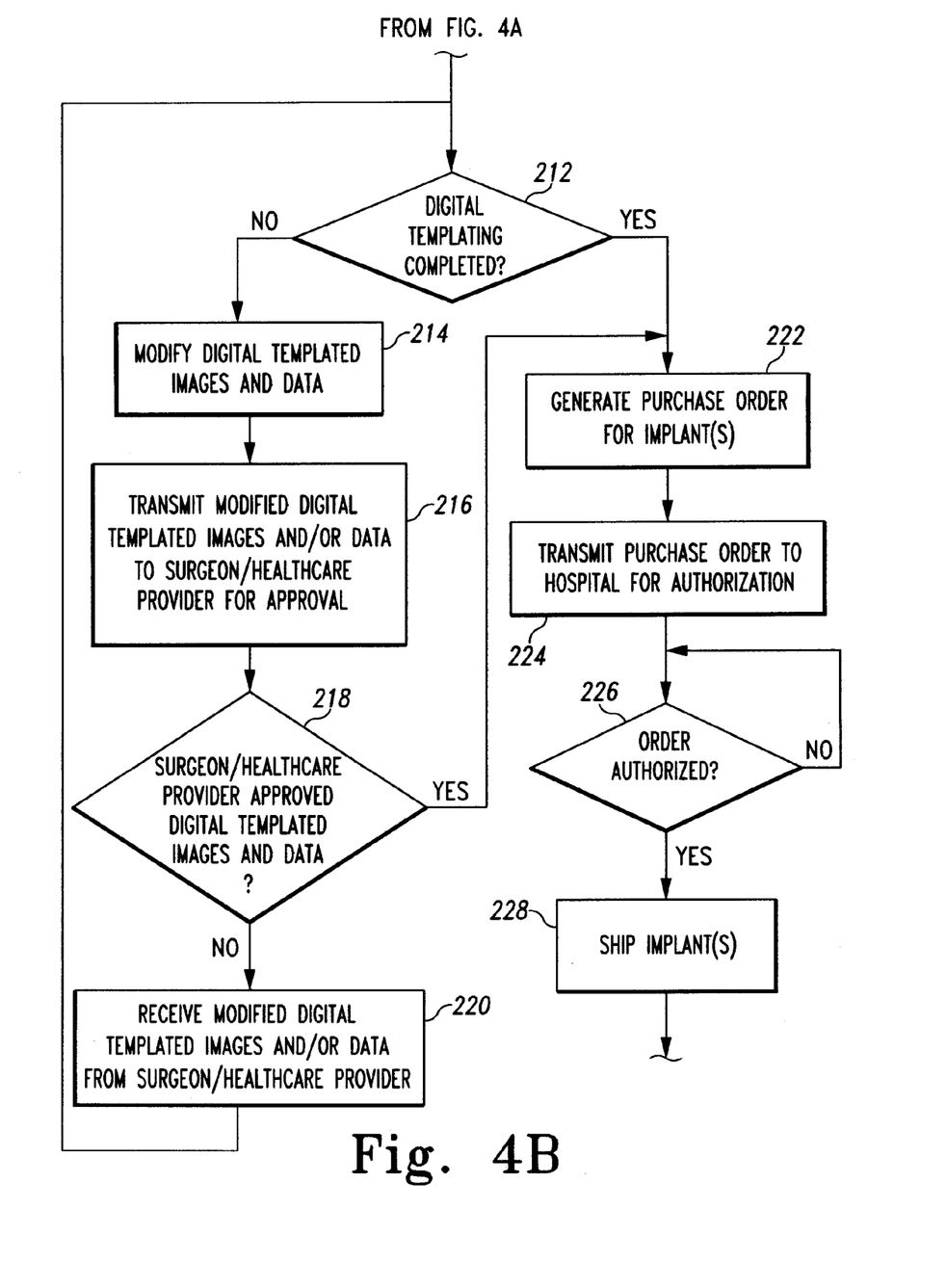

Referring now to FIG. 3, in another embodiment, the hospital network 12 may include a local implant recommendation system 150. In some embodiments, the local implant recommendation system 150 may be similar to the implant recommendation system 40 and may be embodied as any number of computers and/or computing devices, and associated software and/or firmware, configured to perform the implant recommendation functions described herein. For example, the local implant recommendation system 150 may be embodied as one or more computers and/or computing devices having one or more processors (not shown) and one or more memory devices (not shown). Alternatively, the local implant recommendation system 150 may be embodied as software and/or firmware accessible and executable by the surgeon's computer 26. Similar to the implant recommendation system 150, the local implant recommendation system 150 may be used by the surgeon to perform a digital templating procedure on a collection of medical images. Such digital templated medical images may be used by the orthopaedic implant manufacturer network 14 to validate the surgeon's orthopaedic implant selection and pre-operative plan and to ship the selected orthopaedic implants in an automated manner as discussed below in regard to FIGS. 4a-4b.

Referring now to FIG. 4a-4b, in another embodiment, an algorithm 200 for managing inventories of orthopaedic implants begins with a process step 202. Process step 202 is substantially similar to process step 102 of algorithm 100. In process step 202, medical images of a relevant bone or bones of a patient are generated. As described above in regard to algorithm 100, the medical images may include any number of medical images and may be any type of image capable of providing indicia of the relevant bone or bones. For example, the medical images may be embodied as any number of X-ray images, magnetic resonance imaging (MRI) images, computerized tomography (CT) images, or the like. Once generated, the medical images are stored in the database 28 in process step 204. Similar to process step 104 of algorithm 100, the medical images may be stored in association with metadata such as, for example, the patient's name, address, and/or other patient identification data, the surgeon's name or identifier, the healthcare facility's name or identifier, and/or any other type of data useful in determining an orthopedic implant for use with the relevant imaged bone(s).

Once the medical images have been stored, the surgeon may perform a digital templating procedure on the medical images to determine an orthopaedic implant for use with relevant bone(s) of the patient in process step 206. The surgeon may perform the digital templating procedure manually or in an automated manner. For example, the surgeon may operate the local implant recommendation system 150, the surgeon's computer 26, and/or the CAOS system 30 to manually determine the mechanical axis of the relevant bones, locate and mark particular features of the bones, or the like to thereby determine an orthopaedic implant for use with the bone. The surgeon may subsequently retrieve a digital template of the selected orthopaedic implant. The digital template may be retrieved from the memory device (not shown) of the local implant recommendation system 150 or the surgeon's computer, from a database of digital templates stored on the database 28, or downloaded or otherwise obtained from the orthopaedic implant manufacturer's network 14 (e.g., from the implant recommendation system 40). Once retrieved, the surgeon may manually incorporate and position the digital template in the medical images. For example, referring back to FIG. 5, the surgeon may manually superimpose the digital template 300 of the orthopaedic implant into the medical image 302. During the digital templating process, the surgeon may position the digital template 300 in any location and orientation relative to the medical image 302.

Alternatively, the local implant recommendation system 150 may be configured to determine the mechanical axis of the relevant bones, locate particular features of the relevant bones, or the like and select an appropriate orthopaedic implant type and size therefrom. In addition, in some embodiments, the surgeon may provide implant constraint data to the local implant recommendation system 150. If so, the system 150 determines the appropriate orthopaedic implant based on the medical images and the implant constraint data. Further, the implant recommendation system 40 may be configured to determine recommended range of sizes of the orthopaedic implant as discussed above in detail in regard to process step 110 of algorithm 100.

Once the local implant recommendation system 150 has determined the appropriate orthopaedic implant, the system 150 may retrieve a digital template(s) of the orthopaedic implant (e.g., from the database 28 or the implant recommendation system 40) and incorporate the digital template into the medical images. As discussed in more detail above in regard to process step 110 of algorithm 100, the system 150 may use any suitable algorithm (and the implant constraint data in some embodiments) to determine a recommended location and orientation of the orthopaedic implant, as represented by the digital template, with respect to the patient's bone. As such, it should be appreciated that an automated, semi-automated, or manual digital templating procedure may be performed by the surgeon in process step 110.

After the surgeon has completed the digital templating procedure on the medical images in process step 206, the digital templated medical images are transmitted to the implant recommendation system 40 via the communication network 16. In addition, the surgeon may transmit any implant constraint data to the implant recommendation system 40 in process step 210. For example, the digital templated medical images and the constraint data may be transmitted to the system 40 by the local implant recommendation system 150 in response to a command received from the surgeon. Additionally or alternatively, the system 150 may be configured to transmit the digital templated medical images and the constraint data upon conclusion of the digital templating procedure performed by the surgeon in process step 206. Regardless, the digital templated medical images and the constraint data are received by the implant recommendation system 40 in process steps 208 and 210, respectively.

Subsequently, in process step 212, the implant recommendation system 40 determines if the digital templating procedure is completed. As discussed above in regard to process step 118 of algorithm 100, the system 40 may use any suitable algorithm or criteria to determine if the digital templating procedure is complete. For example, in some embodiments, the implant recommendation system 40 may determined if the digital template of the recommended orthopaedic implant is positioned in a valid location and orientation, if the orthopaedic implant selected by the surgeon is a valid orthopaedic implant type and/or size, if any additional adjusts to the digital templated medical images are required, and/or the like.

If the digital templating procedure is determined to be completed, the algorithm 200 advances to process step 222, which is described in detail below. However, if the digital templating procedure is not completed, the implant recommendation system 40 is configured to modify the digital templated medical images and any implant recommendation data in process step 214 as discussed in detail above in regard to process step 120 of algorithm 200. Once modified, the implant recommendation system 40 transmits the modified digital templated medical images and implant recommendation data to the surgeon in process step 216.

In process step 218, the surgeon reviews the modified digital templated medical images and any related implant recommendation data (e.g., a range of implant sizes) to determine if he/she approves of the recommended orthopaedic implant type and size(s) based on the digital templated medical images and implant recommendation data. For example, the surgeon may review the digital templated medical images to determine if the digital template of the orthopaedic implant is properly located with respect to the patient's bone, if the type of recommended orthopaedic implant is correct, if a larger or smaller orthopaedic implant size is more desirable, and/or the like. If the surgeon approves the modified digital templated medical images and the implant recommendation data, an electronic approval is received from the surgeon by the implant recommendation system 40 in process step 218 and the algorithm advances to process step 222, which is described in detail below. The electronic approval may be embodied as any type of data transmittable over the network 16 and capable of providing notification to the systems 40, 42 that the digital templated medical images and recommendation data is approved by the surgeon.

However, if the surgeon does not approve the modified digital templated medical images and the implant recommendation data, the surgeon may further modify the digital templated medical images and/or implant recommendation data and transmit the images and data to the implant recommendation system 40 in processes step 220. Once the modified digital templated medical images and/or recommendation data are received from the surgeon in process step 220, the algorithm 200 loops back to process step 212 wherein the implant recommendation system 40 again determines if the digital templating procedure is completed. As such, the process steps 212, 214, 216, 218, 220 may be repeated until digital templated medical images and/or recommendation data are as desired by the surgeon and/or determined completed by the implant recommendation system 40.

Referring back to process step 212, if the implant recommendation system 40 determines that the digital templating procedure is completed, the algorithm 200 advances to process step 222. In process step 222, a purchase order of the recommended orthopaedic implant(s) is generated. As discussed above in regard to process step 122 of algorithm 100, the purchase order may be generated by either the implant recommendation system 40 or the inventory management system 42. Once generated, the purchase order is transmitted to the hospital network 12 for authorization in process step 224. The purchase order may be transmitted to the hospital network 12 via the communication links 20 or 22, the communication network 16, and the communication link 18. In one particular embodiment, the purchase order is transmitted to an individual, department, or other entity of the healthcare provider (e.g., the hospital) that is responsible for the payment of bills such as, for example, the accounts receivable department of the healthcare provider. Additionally or alternatively, the purchase order may be transmitted to an individual or department that oversees or otherwise monitors orthopaedic surgeries. Regardless, the purchase order is transmitted to the hospital network 12 for authorization by the healthcare provider (e.g., the hospital, the surgeon, the accounts receivable department, or the like) in process step 224.

Once the purchase order has been transmitted to the healthcare provider in process step 224, the implant recommendation system 40 and/or the inventory management system 42 waits for an electronic authorization from the healthcare provider. As discussed above, the electronic authorization may be embodied as any type of data transmittable over the network 16 and capable of providing notification to the systems 40, 42 that the purchase order is authorized. Once the electronic authorization is received from the healthcare provider in process step 226, the orthopaedic implant(s) is timely shipped to the healthcare provider in process step 228. To do so, in some embodiments, the inventory management system 42 is configured to generate a shipping order based on the purchase order as discussed in more detail above in regard to process step 128 of algorithm 100.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. A method for managing inventories of orthopaedic implants, the method comprising:
receiving, by a computing system and over a network, (i) an authorization to retrieve medical images and metadata associated with the medical images from a healthcare provider network and (ii) a location within the healthcare provider network from which the medical images and the metadata can be retrieved;
retrieving, from the location within the healthcare provider network, (i) a medical image of a patient's bone and (ii) surgeon preference data, selected by a healthcare provider that identifies a desired characteristic of an orthopaedic implant, over the network by the computing system;
selecting, by the computing system, a number of orthopaedic implants from an inventory of orthopaedic implants, the inventory of orthopaedic implants comprises a plurality of orthopaedic implants available for selection, the orthopaedic implants being selected based on the medical image and the surgeon preference data;
retrieving, by the computing system, a stored digital template for each of the selected orthopaedic implants from a data repository comprising a plurality of digital templates;
determining, by the computing system, an axis of the patient's bone from the medical image;
performing, by the computing system, a number of digital templating procedures on the medical image to automatically superimpose each digital template of each selected orthopaedic implant onto the medical image in a location and orientation that is automatically selected as a function of the determined axis of the patient's bone and an amount of bone to be resected from the patient's bone during an orthopaedic surgical procedure to generate a number of digital templated images; and
transmitting, by a communication circuit of the computing system, the number of digital templated images generated from the number of digital templating procedures to the healthcare provider over the network using a communication protocol.

2. The method of claim 1, further comprising:
receiving, by the computing system, an electronic approval from the healthcare provider in response to transmitting the number of the digital templated images; and
generating a shipping order by the computing system to ship the selected orthopaedic implants to the healthcare provider in response to receiving the electronic approval.

3. The method of claim 1, wherein transmitting the number of the digital templated images comprises transmitting the number of the digital templated images using a Digital Imaging and Communications in Medicine communication protocol.

4. The method of claim 1, wherein selecting the number of orthopaedic implants based on the medical image comprises selecting a range of orthopaedic implant sizes that satisfy the surgeon preference data.

5. The method of claim 4, wherein selecting the number of orthopaedic implants comprises selecting orthopaedic implants within two sizes of a size of an orthopaedic implant that satisfies the surgeon preference data.

6. The method of claim 4, further comprising generating a shipping order by the computing system to ship the number of orthopaedic implants selected based on the range of orthopaedic implant sizes to the healthcare provider.

7. The method of claim 1, further comprising:
transmitting a purchase order for the selected orthopaedic implants to the healthcare provider over the network by the computing system;
receiving an electronic authorization of the purchase order from the healthcare provider over the network with the computing system; and
generating a shipping order by the computing system to ship the selected orthopaedic implants to the healthcare provider in response to receiving the electronic authorization.

* * * * *